(12) United States Patent
Zwerger et al.

(10) Patent No.: US 9,238,563 B2
(45) Date of Patent: Jan. 19, 2016

(54) APPARATUS FOR DETECTING AN EDGE OF A MATERIAL WEB

(71) Applicants: Lars Zwerger, Augsburg (DE); Wolfgang Krauth, Friedberg (DE); Günter Franz, Biberbach (DE)

(72) Inventors: Lars Zwerger, Augsburg (DE); Wolfgang Krauth, Friedberg (DE); Günter Franz, Biberbach (DE)

(73) Assignee: TEXMAG GMBH VERTRIEBSGESELLSCHAFT, Thalwil (CH)

( * ) Notice: Subject to any disclaimer, the term of this patent is extended or adjusted under 35 U.S.C. 154(b) by 280 days.

(21) Appl. No.: 13/871,834

(22) Filed: Apr. 26, 2013

(65) Prior Publication Data

US 2013/0308427 A1 Nov. 21, 2013

(30) Foreign Application Priority Data

Apr. 27, 2012 (DE) ...................... 20 2012 004 305 U

(51) Int. Cl.
| | |
|---|---|
| *B65H 23/02* | (2006.01) |
| *G01N 29/27* | (2006.01) |
| *G01B 17/06* | (2006.01) |
| *G01S 15/04* | (2006.01) |
| *G01S 15/87* | (2006.01) |
| *G01N 29/11* | (2006.01) |

(52) U.S. Cl.
CPC ............ *B65H 23/0204* (2013.01); *G01B 17/06* (2013.01); *G01N 29/27* (2013.01); *G01S 15/04* (2013.01); *G01S 15/87* (2013.01); *B65H 2553/30* (2013.01); *G01N 29/11* (2013.01); *G01N 2291/0237* (2013.01); *G01N 2291/048* (2013.01); *G01N 2291/105* (2013.01)

(58) Field of Classification Search
CPC ........... B65H 2553/30; B65H 23/0204; B65H 23/0322; G01N 29/27; G01B 17/06
USPC ................. 700/66; 226/45; 73/599, 643, 159; 702/150
See application file for complete search history.

(56) References Cited

U.S. PATENT DOCUMENTS

| | | | | |
|---|---|---|---|---|
| 3,225,988 | A | * | 12/1965 | Drenning ......................... 226/19 |
| 3,323,699 | A | * | 6/1967 | Bricker, Jr. ....................... 226/15 |
| 3,570,624 | A | * | 3/1971 | O'Connor ........................ 73/159 |
| 3,750,624 | A | | 8/1973 | O'Connor et al. |
| 4,066,969 | A | * | 1/1978 | Pearce et al. .................... 367/125 |
| 4,073,007 | A | * | 2/1978 | Boivin ............................ 702/43 |

(Continued)

FOREIGN PATENT DOCUMENTS

| | | |
|---|---|---|
| DE | 202011002054 | 1/2011 |
| WO | 2008/121238 | 10/2008 |

OTHER PUBLICATIONS

EP Search Report issued in European Application Serial No. 13165565.6 on Jul. 2, 2013 3 pages. Machine translation provided by Fast-Trans Translatons, GLTaC, Inc. 3 pages translated.

(Continued)

*Primary Examiner* — Ari M Diacou
(74) *Attorney, Agent, or Firm* — Fish & Richardson P.C.

(57) ABSTRACT

Some aspects relate to an apparatus for detecting an edge of a material web. In some examples, the apparatus comprises an ultrasound sensor which comprises two or more separately readable ultrasound receiver elements and an ultrasound transmitter element, wherein the ultrasound transmitter element is designed and arranged such that it applies an ultrasound measurement signal to two or more of the ultrasound receiver elements.

24 Claims, 10 Drawing Sheets

(56) References Cited

U.S. PATENT DOCUMENTS

| | | | | |
|---|---|---|---|---|
| 4,473,769 A * | 9/1984 | Nguyen | ............... | B06B 1/0692 310/334 |
| 4,493,065 A * | 1/1985 | Sword, Jr. | ...................... | 367/96 |
| 4,901,292 A * | 2/1990 | Schrauwen | ................... | 367/118 |
| 5,126,946 A * | 6/1992 | Ko | ................. | 700/66 |
| 5,166,532 A * | 11/1992 | Brunner | ............... | G01D 5/342 250/227.31 |
| 5,274,573 A * | 12/1993 | Buisker et al. | ............... | 702/103 |
| 5,300,787 A * | 4/1994 | Schrauwen et al. | .......... | 250/548 |
| 5,340,510 A * | 8/1994 | Bowen | ............... | C04B 35/4682 264/272.16 |
| 5,565,627 A * | 10/1996 | Dorr | .............................. | 73/599 |
| 5,803,334 A * | 9/1998 | Patel et al. | ...................... | 226/45 |
| 5,834,877 A * | 11/1998 | Buisker et al. | ................ | 310/322 |
| 6,289,729 B1 * | 9/2001 | Haque et al. | ..................... | 73/159 |
| 7,075,099 B2 * | 7/2006 | Buisker et al. | ........... | 250/559.36 |
| 7,130,245 B2 * | 10/2006 | Okitsu et al. | ................. | 367/125 |
| 7,151,715 B2 * | 12/2006 | Eisen et al. | ................... | 367/129 |
| 7,357,027 B2 * | 4/2008 | Haque et al. | ..................... | 73/597 |
| 7,372,061 B2 * | 5/2008 | Buisker et al. | ........... | 250/559.36 |
| 7,388,317 B2 * | 6/2008 | Asada et al. | ................. | 310/322 |
| 7,411,206 B2 * | 8/2008 | Buisker et al. | ........... | 250/559.36 |
| 7,415,881 B2 * | 8/2008 | Haque et al. | ..................... | 73/597 |
| 8,082,792 B2 * | 12/2011 | Haque et al. | ..................... | 73/598 |
| 8,448,517 B2 * | 5/2013 | Itsumi et al. | ................... | 73/597 |
| 8,789,421 B2 * | 7/2014 | Krauth et al. | ................... | 73/632 |
| 2004/0149940 A1 * | 8/2004 | Buisker et al. | ........... | 250/559.36 |
| 2004/0150155 A1 * | 8/2004 | Okitsu et al. | .................. | 271/262 |
| 2005/0034520 A1 * | 2/2005 | Eisen et al. | ..................... | 73/627 |
| 2006/0048577 A1 * | 3/2006 | Haque et al. | ..................... | 73/599 |
| 2006/0145412 A1 * | 7/2006 | Tagawa et al. | ........... | 271/258.01 |
| 2006/0254360 A1 * | 11/2006 | Haque et al. | ..................... | 73/613 |
| 2007/0029514 A1 * | 2/2007 | Buisker et al. | ........... | 250/559.36 |
| 2007/0241293 A1 * | 10/2007 | Buisker et al. | ........... | 250/559.36 |
| 2008/0088084 A1 * | 4/2008 | Shimazaki | .................... | 271/262 |
| 2008/0289422 A1 * | 11/2008 | Haque et al. | ..................... | 73/599 |
| 2012/0192652 A1 * | 8/2012 | Krauth et al. | ................... | 73/641 |

OTHER PUBLICATIONS

EP Communication pursuant to Article 94(3) for European Application Serial No. 13165565.6 issued Aug. 13, 2013, 5 pages. Machine translation provided by Fast-Trans Translation, GLTaC, Inc. 4 pages translated.

EP Communication pursuant to Article 94(3) for European Application Serial No. 13165565.6 issued on Dec. 2, 2014, 6 pages. Machine translation—Google Translate—4 pages translated.

KR Notice of Preliminary Rejection issued in KR application 10-2013-0047592, on Sep. 18, 2015; Korean 7 pages; English translation 7-pages.

* cited by examiner

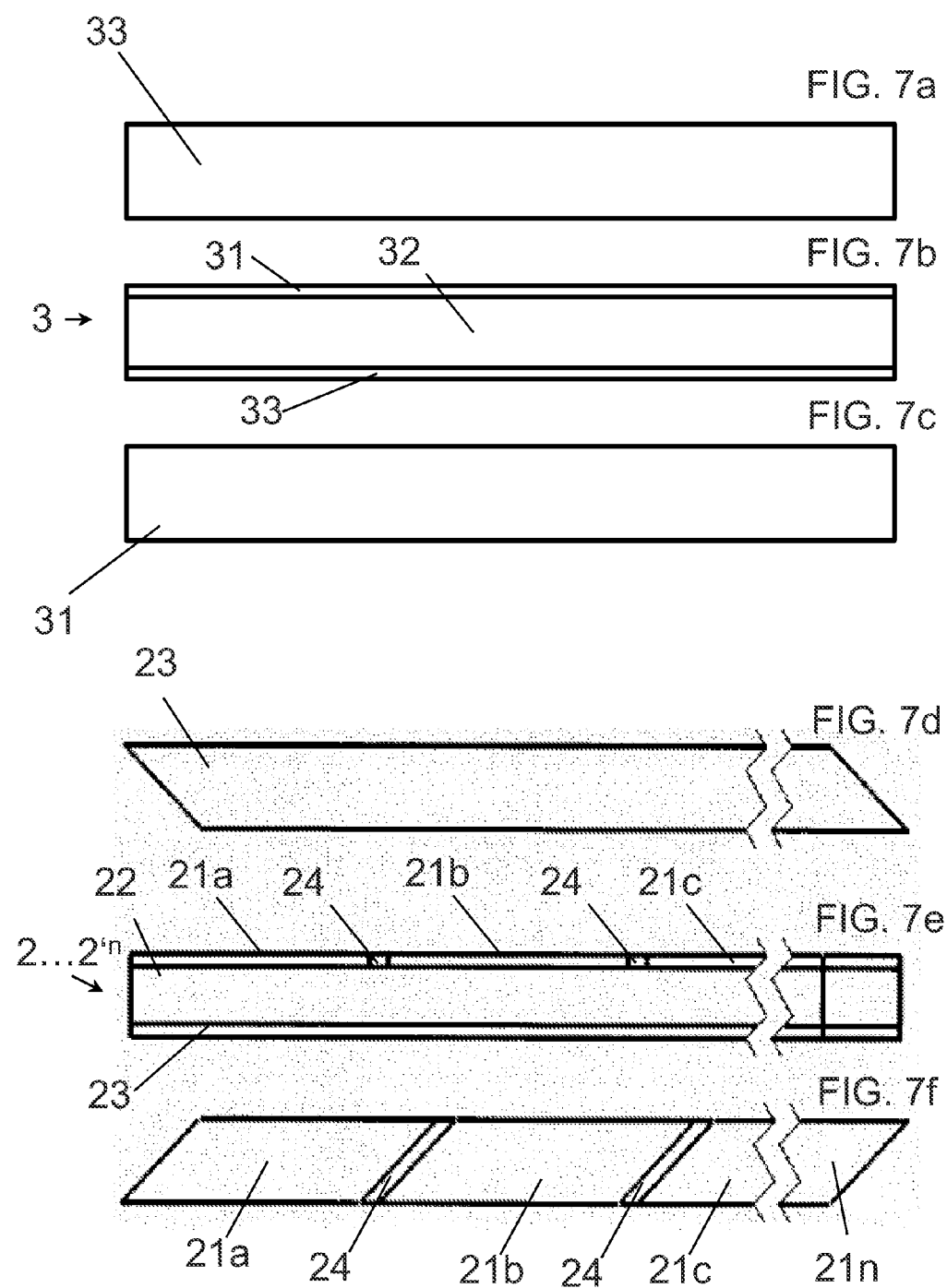

FIG. 9a
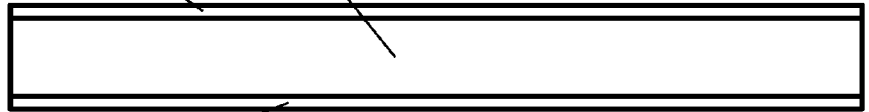
FIG. 9b
FIG. 9c
FIG. 9d
FIG. 9e
FIG. 9f

APPARATUS FOR DETECTING AN EDGE OF A MATERIAL WEB

CLAIM OF PRIORITY

This application claims priority to German Utility Model Application No. 20 2012 004 305.6, filed on Apr. 27, 2012.

TECHNICAL FIELD

The present disclosure relates to an apparatus for detecting a material web by using ultrasound sensors. Such apparatuses are used for contactlessly scanning web edges of paper, material or foil webs, for example. Apparatuses having ultrasound sensors are particularly suitable for transparent or light-sensitive material webs, where there is only a limited possibility of using optical sensors.

BACKGROUND

Apparatuses for detecting the edge of a material web using a plurality of ultrasound sensors are known, as shown in U.S. Pat. No. 7,357,027 B2, for example. In order to provide a certain measurement range, these apparatuses have a multiplicity of individual ultrasound sensors arranged in an array, with each individual ultrasound sensor comprising an ultrasound transmitter element and an ultrasound receiver element. In this arrangement, each ultrasound receiver element has a dedicated associated ultrasound transmitter element which applies an ultrasound signal to said ultrasound receiver element. Such apparatuses require a large number of transmitter and ultrasound receiver elements, which increases the complexity and costs of the apparatus.

SUMMARY

A first aspect relates to an apparatus for detecting an edge of a material web. The apparatus comprises an ultrasound sensor which comprises two or more separately readable ultrasound receiver elements and an ultrasound transmitter element, wherein the ultrasound transmitter element is designed and arranged such that it applies an ultrasound measurement signal to two or more of the ultrasound receiver elements. This makes it possible to simplify the actuation of the apparatus, which increases reliability and can reduce the costs of the apparatus. In addition, it is possible to ensure more homogeneous exposure to sound for the ultrasound receiver elements, since there are no (or fewer) barriers to sound between individual ultrasound receiver elements. These advantages have a particular effect in the case of apparatuses which have an extensive measurement range (for example more than 20 mm) In these apparatuses, a single ultrasound transmitter element can apply an ultrasound measurement signal to a multiplicity of ultrasound receiver elements.

An ultrasound sensor comprises at least the components which are necessary for producing a first ultrasound signal ("ultrasound transmitter element") and for detecting a second ultrasound signal ("ultrasound receiver element"), which is produced by the interaction of the first ultrasound signal with the material web that is to be detected.

An ultrasound receiving element is a component which detects an ultrasound signal by converting an incident ultrasound signal into an electrical signal. Ultrasound receiver element refers to an individually readable component. That is to say that an ultrasound receiver element produces an individual measured value which is dependent on the sound pressure of the incident ultrasound signal and/or that surface area of the ultrasound receiver element which is exposed to sound by the incident ultrasound signal.

An ultrasound transmitter element is a component which produces an ultrasound signal by converting an electrical signal into an emitted ultrasound signal.

Ultrasound transmitter element refers to an individually actuatable component. That is to say that an ultrasound transmitter element produces the emitted ultrasound signal from an individual electrical signal (which may by all means be present at a multiplicity of locations of the ultrasound transmitter element simultaneously, however).

Ultrasound measurement signal refers to an ultrasound signal which can be converted at an ultrasound receiver element into a signal (or a signal component) which can be used for detecting the edge of the material web. By contrast, although an ultrasound disturbance signal is converted into an electrical signal in an ultrasound receiver element, it cannot be used by the apparatus to detect the edge. Disturbance signals arise, by way of example, as a result of undesirable reflections or imperfect focussing of an ultrasound signal.

The portion of the ultrasound receiver element which brings about the conversion from the ultrasound signal to the electrical signal is called an ultrasound transducer element. Correspondingly, the portion of the ultrasound transmitter element which brings about the conversion from the electrical signal to the ultrasound signal is also called an ultrasound transducer element.

An ultrasound sensor can have just one receiver element and ultrasound transmitter element or else a multiplicity of receiver elements and/or ultrasound transmitter elements in order to detect the edge of a material web.

The term material web covers features of a material which have a substantially greater extent in two spatial directions than in the third. In this case, the material web may have cutouts and openings. It is not necessary for the material web to be contiguous either. In particular, the term material web covers fabrics and meshes or else a series of warp threads prior to the introduction of the weft threads of a fabric, which likewise form a material web.

All of these material webs are bounded in one of the two extensive spatial directions by a respective edge which can be detected by using the apparatus. In this case, detection of an edge may merely comprise establishing that there is an edge in a measurement range. Furthermore, detection of an edge may comprise detecting a position of the edge (for example as an offset measured in relation to a stipulated zero point). Detection of an edge of a material web also comprises detecting both edges which bound the material web in a spatial direction. Hence, it is possible to determine a width of the material web or a position for the material web. This also allows a compression or expansion for the material web to be ascertained.

The apparatuses can be used to detect material webs which comprise materials which reflect, absorb or transmit at least a portion of an ultrasound signal. In particular, material webs made of plastic, paper, cardboard or textiles can be detected.

A second aspect relates to an apparatus for detecting an edge of a material web. The apparatus comprises an ultrasound sensor which comprises an ultrasound receiver element and an ultrasound transmitter element, wherein the ultrasound transmitter element comprises an ultrasound transducer element which comprises a piezoelectric composite material.

Piezoelectric composite materials comprise materials in which piezoelectrically active materials (such as piezoelectric ceramics) are integrally connected to "passive" materials (such as particular polymers). Piezoelectric composite materials also comprise piezoelectric ceramics which are integrally connected to piezoelectrically active polymers or other plastics.

A third aspect relates to an apparatus for detecting an edge of a material web. The apparatus comprises an ultrasound sensor which comprises an ultrasound receiver element and an ultrasound transmitter element, wherein the ultrasound receiver element comprises an ultrasound transducer element which comprises a piezoelectric composite material.

The use of a piezoelectric composite material allows greater flexibility in the design of the ultrasound transmitter elements and/or ultrasound receiver elements to be achieved in comparison with conventional full ceramic ultrasound transducer elements. The piezoelectric composite materials can be put into (almost) any forms comparatively easily. In particular, long (for example longer than 20 mm) single-piece ultrasound transducer elements can be manufactured from a piezoelectric composite material. Hence, the apparatuses may be less complex (particularly in the case of a large measurement range) than conventional apparatuses, since, by way of example, the design of the actuating circuit of the apparatus is simplified. In addition, in contrast to the situation in which full ceramic materials are used, the use of piezoelectric composite materials does not require an open-cell porous interface layer into air. Instead, the interface layer can be sealed and smooth. This can lead to improved chemical resistance, can reduce sensitivity to soiling and can render overlying parts superfluous, which can result in a shorter down time and/or maintenance time for the apparatus and thus in lower operating costs.

A fourth aspect relates to an apparatus for detecting an edge of a material web. The apparatus comprises an ultrasound sensor which comprises two or more separately readable ultrasound receiver elements and an ultrasound transmitter element, wherein the two or more ultrasound receiver elements have a common ultrasound transducer element.

A fifth aspect relates to an apparatus for detecting an edge of a material web. The apparatus comprises an ultrasound sensor which comprises an ultrasound receiver element and two or more separately actuatable ultrasound transmitter elements, wherein the two or more ultrasound transmitter elements have a common ultrasound transducer element. The use of a common ultrasound transducer element for a plurality of ultrasound transmitter elements and/or ultrasound receiver elements allows the flexibility of the apparatus to be increased and the complexity of manufacture to be reduced. Particularly for apparatuses having a large measurement range (for example longer than 20 mm), the use of a common ultrasound transducer element means that a severely reduced (in comparison with conventional apparatuses) number of parts is required. This facilitates the design of the apparatus. In addition, it is possible to form the ultrasound transmitter elements and/or ultrasound receiver elements by patterning the electrodes that have been put on the common ultrasound transducer element, for example. This may be an extremely flexible and inexpensive way of providing apparatuses that are customized to various measurement requirements.

A sixth aspect relates to an apparatus for detecting an edge of a material web. The apparatus comprises at least one ultrasound sensor, wherein the ultrasound sensor comprises at least one ultrasound transmitter element and at least one ultrasound receiver element, wherein the ultrasound sensor may be designed to fully cover a measurement range of more than 10 mm perpendicular to the direction of movement of the material web, in which measurement range the edge of the material web can be detected, and wherein the ultrasound transducer element of the ultrasound transmitter element and/or of the ultrasound receiver element is of integral design and wherein the ultrasound transducer element of the ultrasound transmitter element and/or of the ultrasound receiver element may be designed to fully cover a measurement range of more than 10 mm perpendicular to the direction of movement of the material web, in which measurement range the edge of the material web can be detected.

The apparatus for detecting an edge of a material web may have a plurality of integral ultrasound transducer elements at the transmitter or receiver end which each fully cover a measurement range of more than 10 mm perpendicular to the direction of movement of the material web, in which measurement range the edge of the material web can be detected.

The term integral denotes an integrated element (which does not exclude the integrated element being assembled from a plurality of parts), with the element being able to contain a composite material. By contrast, a multiplicity of discrete ultrasound transducer elements are used in conventional apparatuses in order to cover a measurement range.

Embodiments of the first to sixth aspects may comprise one or more of the following features.

The one or more ultrasound receiver elements may be arranged such that the material web can pass between the one or more ultrasound transmitter elements and one or more ultrasound receiver elements, with the result that the one or more ultrasound transmitter elements and the one or more ultrasound receiver elements are arranged on different sides of the material web. In this case, each ultrasound receiver element detects a portion of the ultrasound signal which is passing the material web (additionally, it is also possible for that portion of the ultrasound signal which is transmitted by the material web to be detected) in order to detect an edge of the material web.

Alternatively, the one or more ultrasound transmitter elements and the one or more ultrasound receiver elements may also be arranged on the same side of the material web. In this case, each ultrasound receiver element detects a portion of the ultrasound signal that is reflected by the material web. It is also possible for one or more ultrasound transmitter elements and one or more ultrasound receiver elements to be arranged on both sides of the material web in order to detect reflected and passing portions (and sometimes transmitted portions) of the ultrasound signal.

Alternatively, an ultrasound transmitter element may be designed likewise to act as an ultrasound receiver element. By way of example, a reflector can be provided which reflects an ultrasound signal that is emitted by an ultrasound transmitter element, as a result of which the reflected signal can be detected on the ultrasound transmitter element, which therefore acts as an ultrasound receiver element.

The ultrasound sensor may comprise one, two, three, four or more than four ultrasound receiver elements.

The ultrasound transmitter element may be designed such that it applies an ultrasound measurement signal to three or four of the ultrasound receiver elements.

The outer contour of at least one of the transmitter elements and/or receiver elements may comprise at least one arc segment side and at least one flattened side. This allows the number of elements required for covering a particular measurement range to be reduced.

Each ultrasound receiver element may have an associated measurement range in which it can detect the edge of the material web, wherein the measurement ranges can directly adjoin or overlap one another in a direction of measurement.

The apparatus may also comprise a housing which comprises a first and a second arm, wherein the one or more ultrasound transmitter elements are arranged on the first arm and the one or more ultrasound receiver elements are arranged on the second arm.

The one or more ultrasound receiver elements may be designed to detect the edge of the material web in a measurement range of more than 10 mm perpendicular to a direction of movement of the material web.

The one or more ultrasound receiver elements may be designed to detect the edge of the material web in a measurement range of more than 20 mm perpendicular to a direction of movement of the material web.

The one or more ultrasound transmitter elements and the one more ultrasound receiver elements may comprise ultrasound transducer elements which comprise one or more piezoelectric composite materials. The piezoelectric composite materials may comprise a polymer and a piezoelectric ceramic. The polymer may be selected from a list comprising epoxy resins and polyurethanes. The piezoelectric composite materials may comprise a 1-3-piezoelectric composite or a 2-2-piezoelectric composite. The piezoelectric composite materials may comprise bars of a piezoelectric ceramic embedded in a polymer. The piezoelectric composite materials may comprise lead zirconate titanate. The piezoelectric composite materials may comprise piezoelectric fibre composite materials which contain bundles of piezoelectric ceramic fibres infiltrated with a polymer (for example an epoxy resin or polyurethane) and thus form a piezoelectric composite material.

An ultrasound transducer element of the one or more ultrasound receiver elements and/or of the one or more ultrasound transmitter elements may be of two-dimensional design. A two-dimensional element has a substantially greater extent in two spatial directions than in the third. By way of example, the ultrasound transducer element may be plate-like, with the outline of the plate-like ultrasound transducer element being able to be chosen arbitrarily. By way of example, the outline may be rectangular or round.

The apparatus may comprise two or more separately readable ultrasound receiver elements or two or more separately actuatable ultrasound transmitter elements, wherein the two or more ultrasound receiver elements and/or the two or more ultrasound transmitter elements may have a common ultrasound transducer element.

The ultrasound sensor may be designed to fully cover a measurement range of more than 10 mm perpendicular to the direction of movement of the material web, in which measurement range the edge of the material web can be detected, and an ultrasound transducer element of the one or more ultrasound transmitter elements and/or of the one or more ultrasound receiver elements may be of integral design.

Opposite surface areas of the ultrasound transducer element of the one or more ultrasound receiver elements and/or of the one or more ultrasound transmitter elements may be provided with metallizations in order to make electrical contact with the ultrasound transducer element. The metallizations of the ultrasound transducer element may be designed such that a side of the ultrasound transducer element that faces the one or more ultrasound transmitter elements has two or more non-contiguous receiver regions formed on it which can be read separately in order to form the two or more ultrasound receiver elements. In this case, each ultrasound receiver element comprises one of the receiver regions as a first electrode, a portion of the ultrasound transducer element which is situated below the receiver region (the patterned metallization being situated on the top of the ultrasound transducer element) as an active element (which converts an ultrasound signal into an electrical signal) and the (or a portion of the) metallization which is averted from the ultrasound transmitter element as a second electrode.

The metallizations of the ultrasound transducer element may be designed such that a side of the ultrasound transducer element that faces the one or more ultrasound receiver elements has two or more non-contiguous transmitter regions formed on it which can be actuated separately in order to form the two or more ultrasound transmitter elements. In this case, each ultrasound transmitter element comprises one of the transmitter regions as a first electrode, a portion of the ultrasound transducer element which is situated below the transmitter region (the patterned metallization being situated on the top of the ultrasound transducer element) as an active element (which converts an electrical signal into an ultrasound signal) and the (or a portion of the) metallization which is averted from the ultrasound receiver element as a second electrode.

The formation of a plurality of receiver and/or transmitter regions makes it a simple matter to attain a flexible configuration for a measurement range of the apparatus in order to attain a measurement sensitivity that is customized to a predetermined measurement task. By way of example, the receiver regions may be designed such that the edge to be detected in the entire measurement range is simultaneously situated above two or above three receiver regions when the apparatus is operated.

The receiver regions may be designed such that measurement ranges of the various receiver regions overlap. By way of example, the receiver regions may be designed such that the measurement ranges of two, three or more receiver elements overlap in the entire measurement range or in a portion of the measurement range.

The receiver regions may be designed such that particular sections of the measurement range are equipped with a greater density of receiver regions than the rest of the measurement range of the apparatus.

The transmitter and/or receiver regions may be of equal area to some extent. The transmitter and/or receiver regions can partially or completely cover a side of the ultrasound transducer element on which they are situated. If the complete coverage of a side of the ultrasound transducer element with transmitter and/or receiver regions of equal area is not possible, one or more marginal regions of the side can have transmitter and/or receiver regions placed in it/them which are not of equal area with the remainder of the transmitter and/or receiver regions. The transmitter and/or receiver regions may have a rectangular or polygonal outline. The transmitter and/or receiver regions may have an outline which is formed by two or more rectangles or parallelograms.

The two or more non-contiguous receiver regions and/or transmitter regions can be formed by cutouts in the metallization. The cutouts can run partly or fully obliquely, perpendicularly or parallel to a direction of movement of the material web. Alternatively, cutouts may run in meandering fashion.

The ultrasound sensor may have more than five or more than ten separately readable ultrasound receiver elements and/or ultrasound transmitter elements, and the more than five or more than ten ultrasound receiver elements and/or ultrasound transmitter elements may have a common ultrasound transducer element.

The apparatus may also comprise a controller, the controller being designed to operate the transmitter elements and ultrasound receiver elements. The apparatus may comprise an evaluation circuit which is communicatively coupled to the ultrasound receiver elements (and optionally to the ultrasound transmitter elements) and is designed to ascertain a position for the edge of the material web from measurement signals that are received by the ultrasound receiver elements.

The apparatus may comprise an evaluation circuit which is communicatively coupled to the ultrasound receiver elements (and optionally to the ultrasound transmitter elements) and is designed to ascertain a position for a second edge of the material web from measurement signals that are received by the ultrasound receiver elements.

The apparatus may comprise an evaluation circuit which is communicatively coupled to the ultrasound receiver elements (and optionally to the ultrasound transmitter elements) and is designed to ascertain the width of the material web from measurement signals that are received by the ultrasound receiver elements.

The apparatus may also comprise a correction apparatus which is designed to alter the position of the edge of the material web on the basis of a comparison of a position signal produced by the evaluation circuit with a setpoint position signal.

The apparatus may comprise means for guiding the material web, wherein the ultrasound sensor is arranged such that it can detect the edge of a material web in a predetermined measurement range.

BRIEF DESCRIPTION OF THE FIGURES

FIG. 7a to FIG. 7f show various schematic views of transmitter and ultrasound receiver elements.

FIG. 9a to FIG. 9f show various schematic views of transmitter and ultrasound receiver elements.

DETAILED DESCRIPTION

Figure 1:
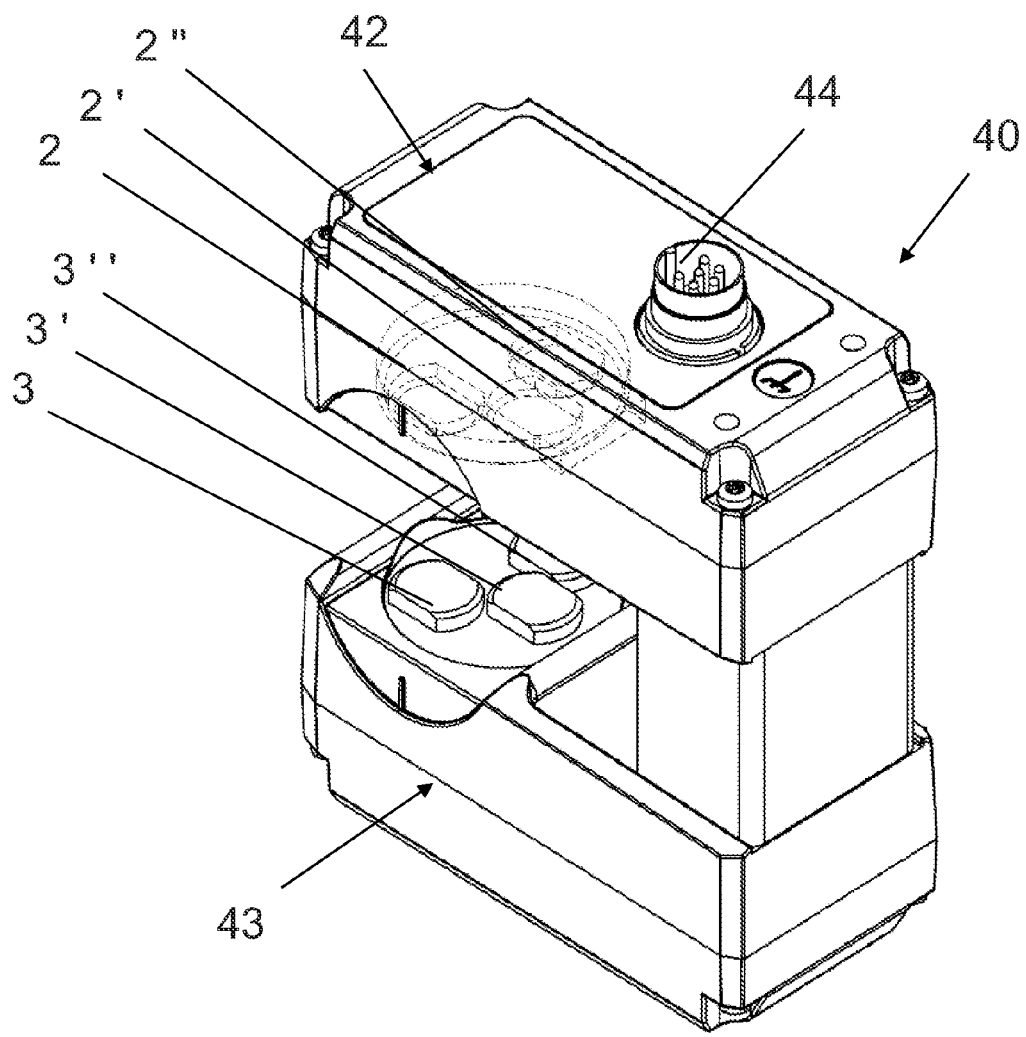
FIG. 1 shows a perspective view of a known apparatus for detecting the position of a material web.

FIG. 1 shows a perspective view of a conventional apparatus 40 for detecting an edge of a material web. The apparatus comprises a housing having two arms 42, 43 which form a U-shaped profile. During operation, an edge of a material web passes through the space which is surrounded by the two arms 42, 43. Opposite arms each have a plurality (in FIG. 1 three) of discrete ultrasound receiver elements 2, 2', 2" and discrete ultrasound transmitter elements 3, 3', 3" of an ultrasound sensor arranged on them, wherein each ultrasound transmitter element 3, 3', 3" applies an ultrasound measurement signal to a respective opposite ultrasound receiver element 2, 2', 2".

When the material web now moves between the two arms 42, 43 of the apparatus 40, the material web prevents a portion of the ultrasound signal that is emitted by the ultrasound transmitter elements 3, 3', 3" from reaching the associated ultrasound receiver element 2, 2', 2". This reduces an amplitude of a measurement signal from the respective ultrasound receiver element 2, 2', 2". The use of a certain number of ultrasound receiver elements 2, 2', 2" and the suitable arrangement thereof make it possible to detect an edge (or the position thereof) of the material web from the measurement signals for the ultrasound receiver elements 2, 2', 2".

Figure 2:
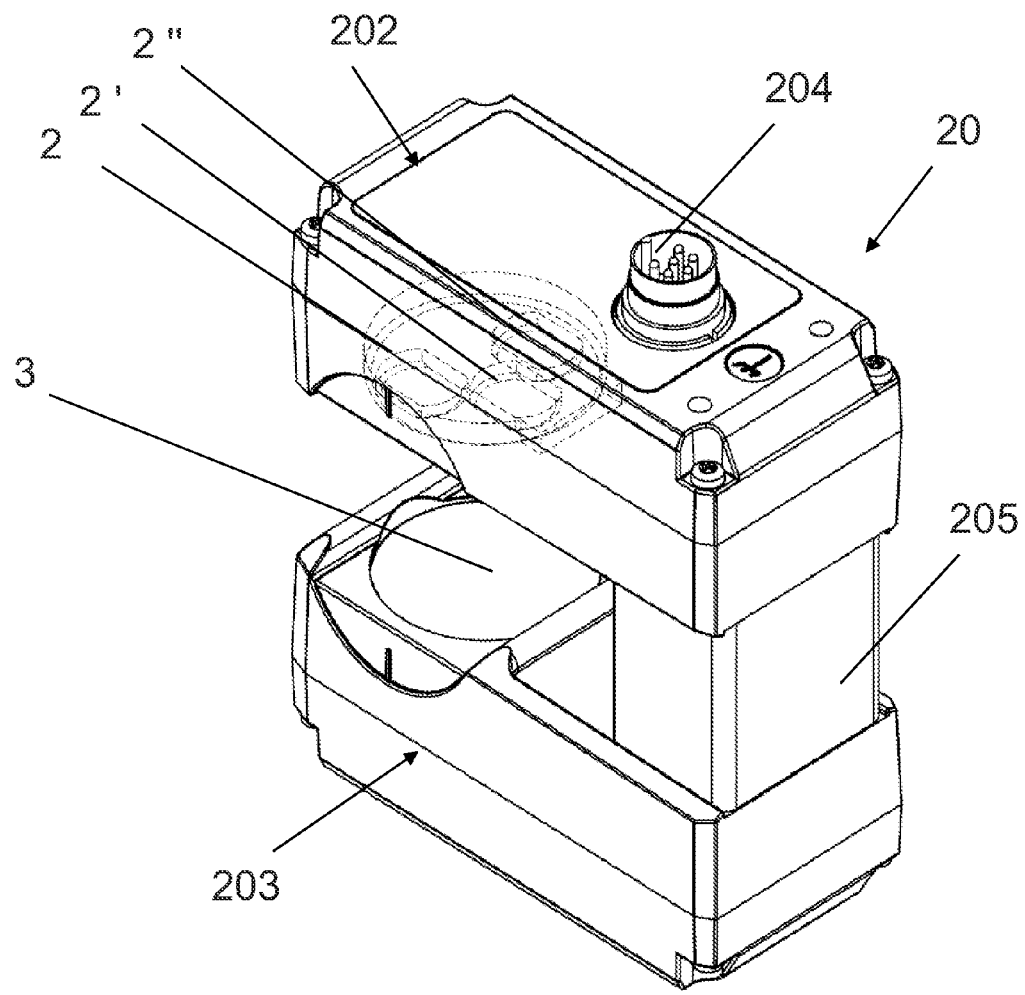
FIG. 2 shows a perspective view of an apparatus for detecting the position of a material web.

FIG. 2 shows an apparatus 20 for detecting an edge of a material web. The apparatus comprises a housing 205 which has a first and a second arm 202, 203. The first arm 202 has a plurality (in FIG. 2 three) of ultrasound receiver elements 2, 2', 2" arranged on it which can each be read individually in order to detect the edge of the material web. The second arm 203 has an individual single ultrasound transmitter element 3 arranged on it. The measurement signals that are read can be tapped off via output 204 for further processing.

Alternatively, the apparatus may also comprise just one arm on which the ultrasound transmitter element and the plurality of ultrasound receiver elements are arranged. In this case, the ultrasound transmitter element and the plurality of ultrasound receiver elements are arranged such that a portion of the ultrasound signal that is emitted by the ultrasound transmitter element is reflected back by the material web onto the plurality of ultrasound receiver elements when the material web is situated in the measurement range of the apparatus. In addition, apparatuses which comprise two arms and in which each arm has an ultrasound transmitter element and a plurality of ultrasound receiver elements arranged on it are possible.

Alternatively, an ultrasound transmitter element may be designed likewise to act as an ultrasound receiver element. By way of example, a reflector can be provided which reflects an ultrasound signal that is emitted by an ultrasound transmitter element, with the result that the reflected signal can be detected on the ultrasound transmitter element, which therefore acts as an ultrasound receiver element. By way of example, the ultrasound transmitter element which is also acting as an ultrasound receiver element can be arranged on the first arm, and the reflector can be arranged on the opposite arm.

The apparatus 20 shown in FIG. 2 has just a single ultrasound transmitter element 3 which applies an ultrasound measurement signal to a plurality of ultrasound receiver elements 2, 2', 2" (in FIG. 2 three). Therefore, a single ultrasound transmitter element 3 has a plurality of associated ultrasound receiver elements 2, 2', 2". The arrangement of the individual ultrasound transmitter elements and ultrasound receiver elements is not limited to the arrangement shown in FIG. 2 with one ultrasound transmitter element and three ultrasound receiver elements. Alternatively, a single ultrasound transmitter element can apply an ultrasound measurement signal to four or more, five or more or ten or more ultrasound receiver elements. It is also possible for the apparatus to have a plurality of ultrasound transmitter elements which each apply an ultrasound measurement signal to more than one ultrasound receiver element (for example two, three or four). One possible embodiment of the ultrasound transmitter element 3 comprises the use of an ultrasound transducer element which comprises a piezoelectric composite material. Details in this regard are described in connection with FIG. 7 to FIG. 9.

In the apparatus 20 shown in FIG. 2, a single ultrasound transmitter element 3 applies sound to a plurality of ultrasound receiver elements 2, 2', 2" which are in the form of discrete components. That is to say that each ultrasound receiver element 2, 2', 2" has a dedicated ultrasound transducer element and has appropriate electrodes. Alternatively, as shown in connection with FIG. 7 to FIG. 9, a plurality of ultrasound receiver elements can be integrated. By way of example, two or more ultrasound receiver elements may have a common ultrasound transducer element and the two or more ultrasound receiver elements can be formed by suitable patterning of the electrodes of the common ultrasound transducer element.

Figure 3:
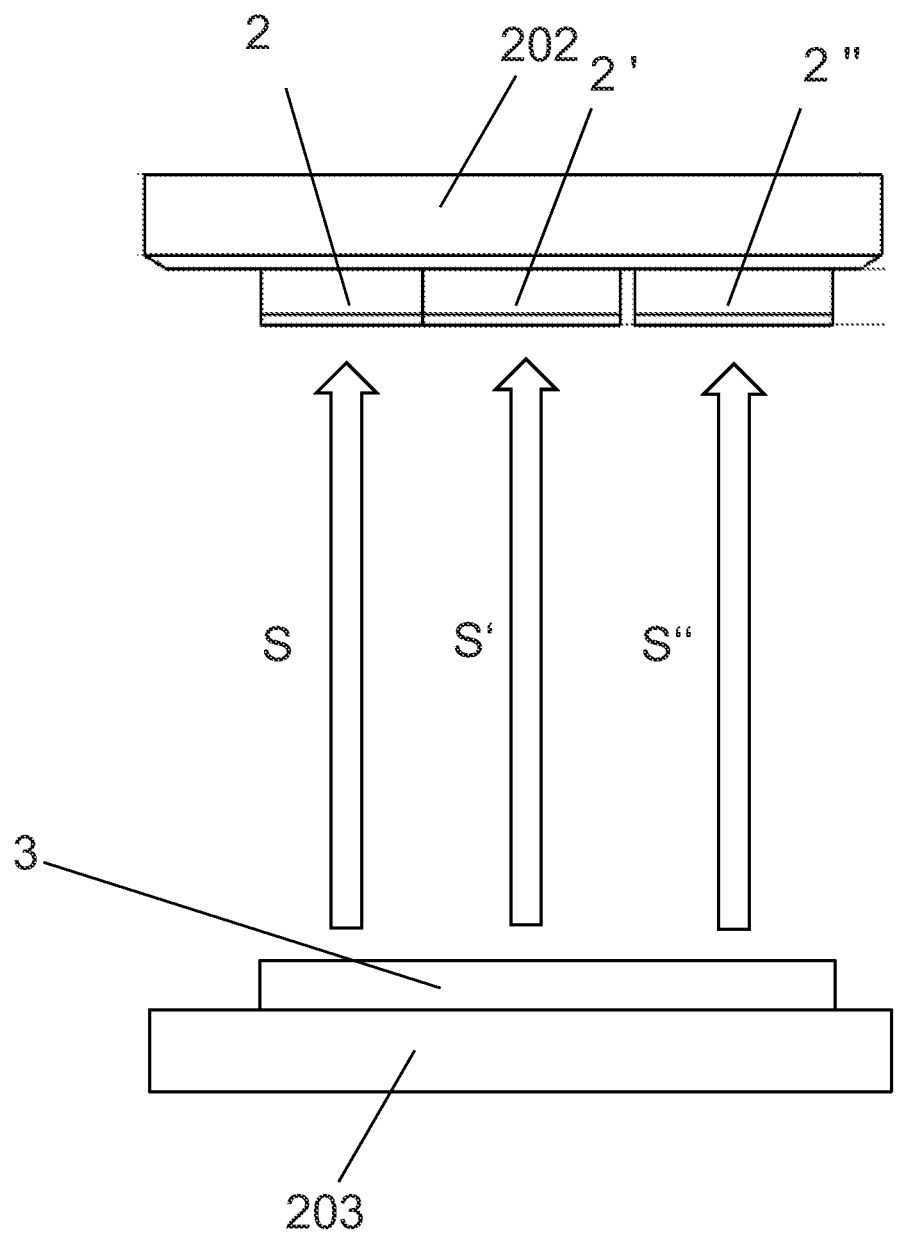
FIG. 3 shows a schematic sectional image through the apparatus shown in FIG. 2.

FIG. 3 shows a schematic sectional image through the apparatus shown in FIG. 2. This clarifies that the individual ultrasound transmitter element 3 applies a respective measurement signal S, S', S" to three ultrasound receiver elements 2, 2', 2".

Figure 4:
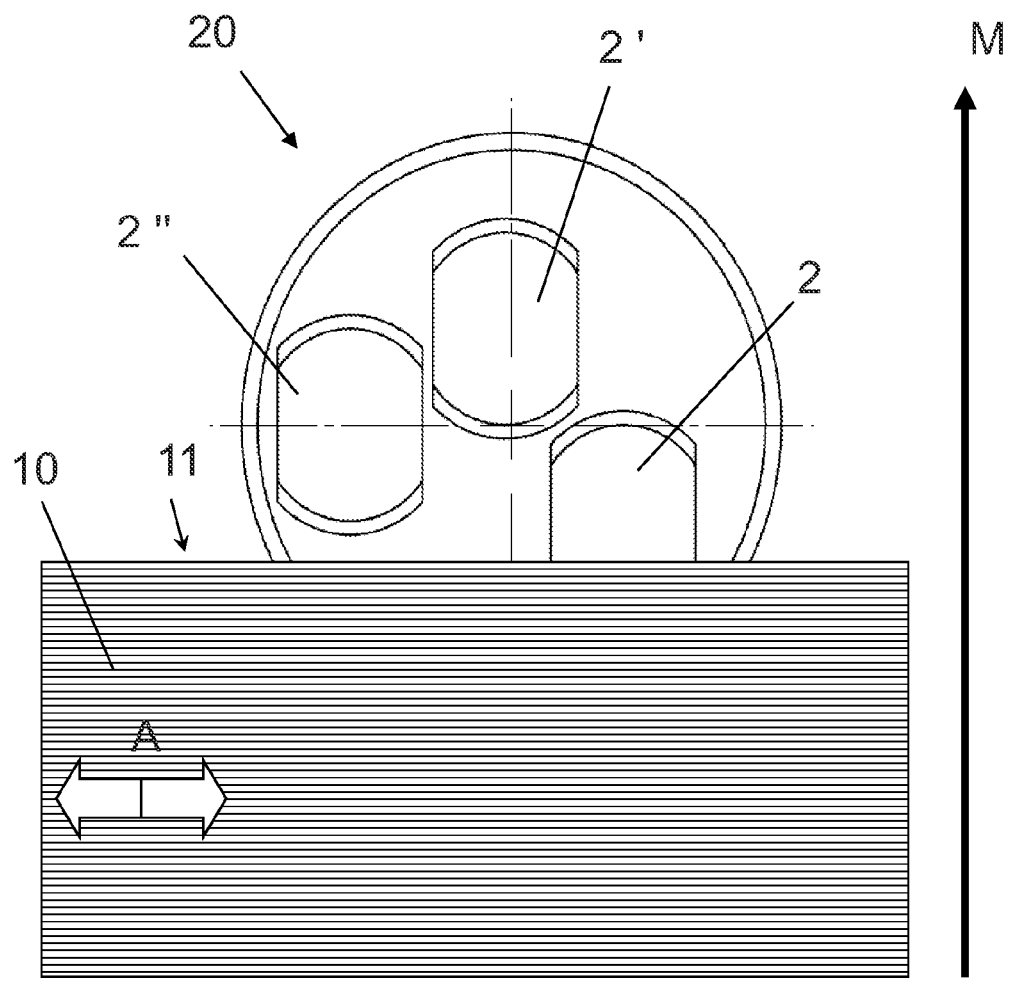
FIG. 4 shows a schematic plan view of the ultrasound receiver elements of the apparatus shown in FIG. 2.

FIG. 4 shows a schematic view of the ultrasound receiver elements 2, 2', 2" of the apparatus 20 shown in FIG. 2. In addition, FIG. 4 shows a material web 10 for which the edge 11 is intended to be detected. Usually, the material web moves in a direction of movement A while the edge 11 of the material web 10 is being detected. However, it is also possible for the edge 11 to be detected when the material web 10 is not moving.

As can be seen in FIG. 4, the material web 10 sweeps over the ultrasound receiver element 2 to some extent, while the remainder of the ultrasound receiver elements 2', 2" are not swept over. The ultrasound transmitter element 3 (not shown in FIG. 4) is situated perpendicular to the plane of the drawing in the direction of the observer and sends ultrasound signals in the direction of the ultrasound receiver elements 2, 2', 2".

Hence, the proportion of the ultrasound signal emitted by the ultrasound transmitter element 3 which reaches the ultrasound receiver elements 2, 2', 2" is reduced by the presence of the material web, since a portion of the emitted ultrasound signal is reflected and/or absorbed by the material web. The physical arrangement of the ultrasound receiver elements 2, 2', 2" means that this reduction in the ultrasound signal (insofar as the edge 11 of the material web is situated inside a measurement range) results in an uneven reduction in the measurement signal from the various ultrasound receiver elements 2, 2', 2". Thus, the measurement signal from the ultrasound receiver elements 2', 2" is not influenced by the presence of the material web 10 in FIG. 4, while the measurement signal from the ultrasound receiver element 2 is reduced.

Therefore, it is possible to infer from the reduction in the measurement signal that the edge 11 of the material web 10 is situated inside the measurement range. Furthermore, it is also possible to determine the position of the edge 11 of the material web 10 in the measurement range. Thus, from the reduction in the measurement signal from the ultrasound receiver element 2 to a fraction of the measurement signal when the material web 10 is absent, it is possible to ascertain what proportion of the surface area of the ultrasound receiver element 2 is swept over by the material web 10. This means that the position of the edge 11 is certain. Since the ultrasound receiver elements 2, 2', 2" in FIG. 4 are arranged such that their measurement ranges directly adjoin one another (not shown in FIG. 4) in the direction of measurement M, it is possible to determine the position of the edge 11 of the material web 10 in an entire measurement range. Alternatively, the measurement ranges of the ultrasound receiver elements 2, 2', 2" may also overlap. This makes it possible to ensure that the position of the edge 11 of the material web 10 can be reliably detected in the boundary region of the individual ultrasound receiver elements 2, 2', 2".

The apparatus 20 shown in FIG. 2 to FIG. 4 may have a measurement range of more than 10 mm, more than 20 mm or more than 50 mm. It is therefore possible to provide a measurement range which sweeps over the complete width of a material web. Hence, it is possible for both edges of a material web to be detected. From this information, it is possible to ascertain not only the position of the material web but also the width of a material web. Alternatively, an expansion or compression of the material web can be ascertained by comparing an ascertained width of the material web with a setpoint width of the material web.

Frequently, the direction of measurement of the apparatus is situated perpendicular to a direction of movement of the material web (or perpendicular to the position of an edge of the material web). However, it is also possible to choose a direction of measurement which is situated obliquely with respect to the direction of movement of the material web. This may involve a suitable arrangement of the ultrasound receiver elements (for example rotation of the arrangement shown in FIG. 4 through a particular angle). Alternatively, an evaluation circuit of the apparatus may be configured such that a direction of measurement obliquely with respect to the direction of movement of the material web is determined.

Figure 5:
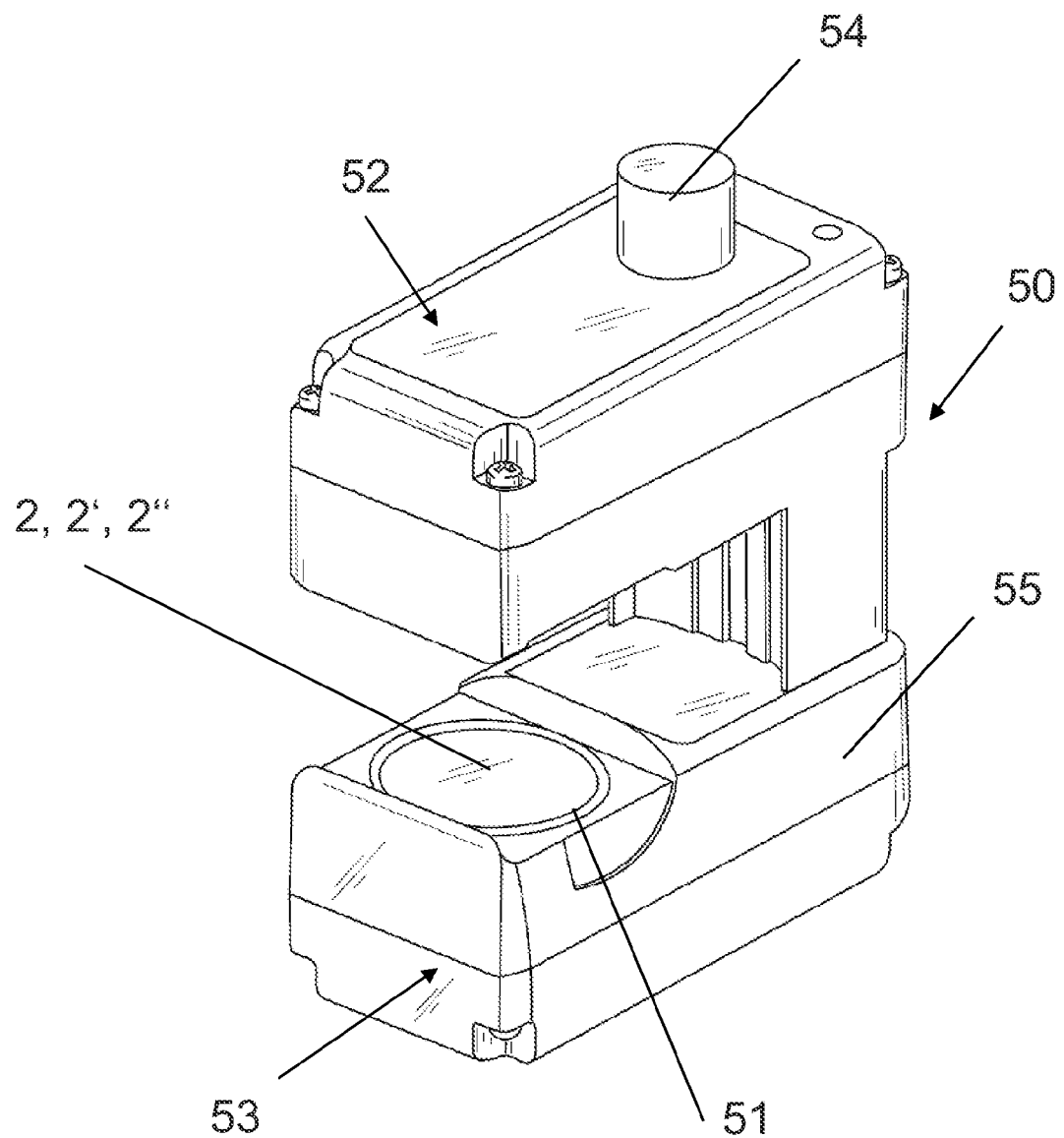
FIG. 5 shows a perspective view of an apparatus for detecting the position of a material web.

FIG. 5 shows a further apparatus 50 for detecting an edge of a material web. Again, the apparatus 50 comprises a housing having two arms 52, 53 on which a plurality of ultrasound receiver elements 2, 2', 2" and an ultrasound transmitter element (not shown in FIG. 5) are arranged. The plurality of ultrasound receiver elements 2, 2', 2" have a common ultrasound transducer element. In addition or alternatively, the apparatus 50 may also comprise a plurality of ultrasound transmitter elements which have a common ultrasound transducer element. One possible embodiment of such ultrasound transmitter elements and/or ultrasound receiver elements comprises the use of a transducer element which comprises a piezoelectric composite material. Details in this regard are described in connection with FIG. 7 to FIG. 9.

In FIG. 5, the ultrasound receiver elements 2, 2', 2" are integrated in a single component 51. This integration is simplified, since the use of a common ultrasound transducer element also allows the remainder of the proportions of the ultrasound receiver elements 2, 2', 2" to be manufactured as an integrated component. It is thus possible for patterning of the electrodes which are put onto the common transducer element to be customized such that the individual ultrasound receiver elements 2, 2', 2" are formed. The individual ultrasound receiver elements 2, 2', 2" can then be read separately. The measurement signal can be provided via an output 54 for further processing.

As FIG. 5 shows, the integrated component which contains the ultrasound receiver elements 2, 2', 2" can be provided with a smooth surface and flush-mounted in the housing 55. The integrated component in FIG. 5 has a round outline, but other shapes of outline are also possible, for example a rectangular outline. The common ultrasound transducer element can, as FIG. 5 shows, cover three ultrasound receiver elements 2, 2', 2". However, it is also possible for two ultrasound receiver elements to have a common ultrasound transducer element. In addition, four or more, five or more or ten or more ultrasound receiver elements may have a common ultrasound transducer element. Hence, measurement ranges of more than 10 mm, more than 20 mm or more than 50 mm can be implemented.

Just as described in connection with FIG. 5 in relation to the ultrasound receiver elements, it is also possible for two or more ultrasound transmitter elements to have a common ultrasound transducer element.

Figure 6:
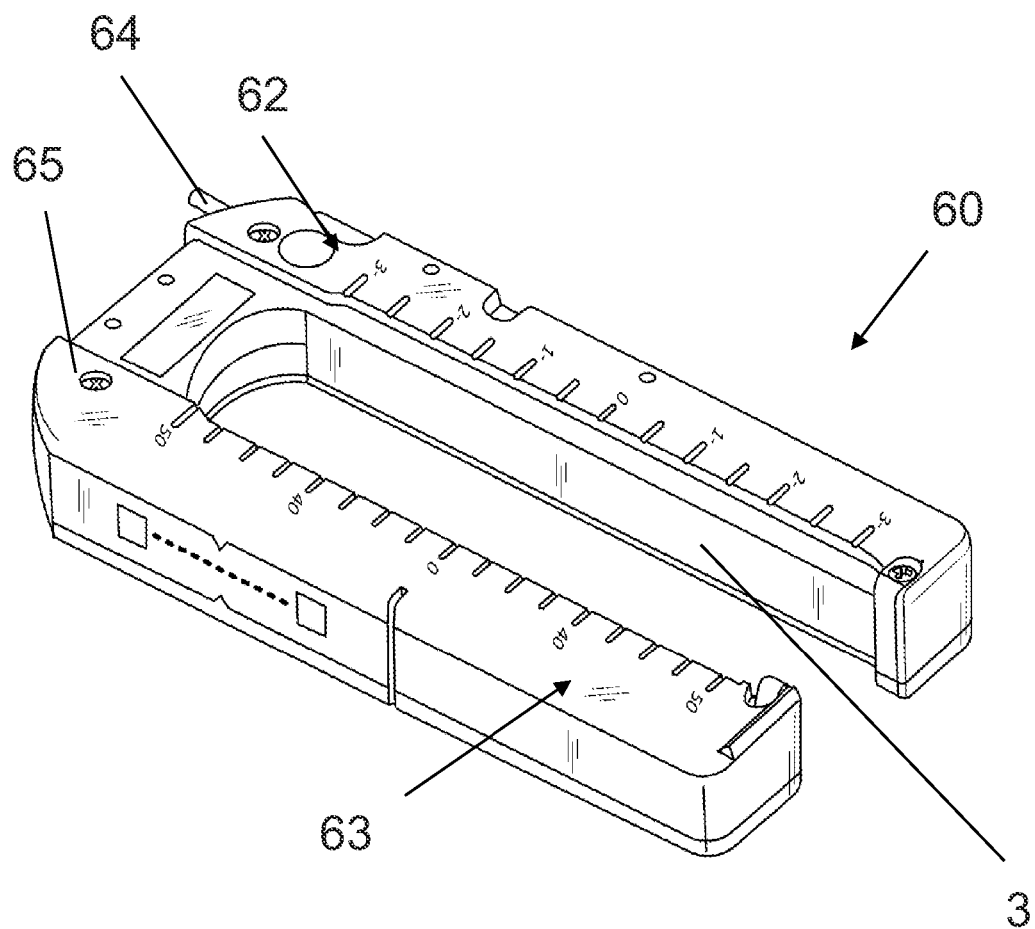
FIG. 6 shows a perspective view of an apparatus for detecting the position of a material web.

FIG. 6 shows a further apparatus 60 for detecting an edge of a material web. The apparatus 60 comprises at least one ultrasound sensor, wherein the ultrasound sensor comprises an ultrasound transmitter element 3 and an ultrasound receiver element (not shown in FIG. 6), wherein an ultrasound transducer element of the ultrasound transmitter element is of integral design and wherein the ultrasound transducer element of the ultrasound transmitter element is designed to fully cover a measurement range of more than 10 mm perpendicular to the direction of movement of the material web, in which measurement range the edge of the material web can be detected. An ultrasound transducer element of the ultrasound receiver element may also be of integral design in the same manner.

Alternatively, an apparatus as shown in FIG. 6 may contain a plurality of integral ultrasound transducer elements which are each designed to fully cover a measurement range of more than 10 mm perpendicular to the direction of movement of the material web. By way of example, the measurement range can cover more than 25 or more than 50 mm in a direction of measurement perpendicular to the direction of movement of the material web.

It is also possible, as shown in connection with FIG. 7 to FIG. 9, for each of the integral ultrasound transducer elements to have two or more ultrasound transmitter elements and/or ultrasound receiver elements arranged on it.

The apparatus 60 shown in FIG. 6 has a housing 65 which contains two arms 62, 63. The ultrasound transmitter element and ultrasound receiver element are each mounted on different arms. The direction of measurement of the apparatus in FIG. 6 runs along the extent of the arms 62, 63.

The integral ultrasound transducer element at the transmitter end can, as described in connection with FIG. 5, have two or more ultrasound transmitter elements formed on it. In addition or alternatively, the integral ultrasound transducer element at the receiver end can, as likewise described in connection with FIG. 5, have two or more ultrasound receiver elements formed on it. However, both the transmitter end and the receiver end can also have a single ultrasound transmitter element or ultrasound receiver element formed on them.

The ultrasound sensor in FIG. 6 may be designed to fully cover a measurement range of more than 20 mm or more than 50 mm perpendicular to the direction of movement of the material web. These large measurement ranges can also be implemented by using a single-piece ultrasound transducer element at the transmitter and/or receiver end. Alternatively, it is also possible for these measurement ranges to be swept over by two or more adjoining or overlapping measurement ranges of 10 or more millimeters, the ultrasound transducer elements at the transmitter and/or receiver end in each measurement range being in a single piece.

As FIG. 6 shows, the ultrasound transmitter element 3 is integrated in an elongate, rectangular component. One possible embodiment of single-piece ultrasound transducer elements comprises the use of a piezoelectric composite material in the ultrasound transducer element. Details in this regard are described in connection with FIG. 7 to FIG. 9. The measurement signals from the apparatus 60 can be read via an output 64.

FIG. 7 to FIG. 9 show examples of single-piece ultrasound transducer elements and a plurality of ultrasound transmitter elements and ultrasound receiver elements having a common ultrasound transducer element. The figures also show arrangements of ultrasound transmitter elements and ultrasound receiver elements in which a single ultrasound transmitter element applies an ultrasound measurement signal to two or more ultrasound receiver elements.

The ultrasound transmitter elements and ultrasound receiver elements in FIG. 7 to FIG. 9 may contain ultrasound transducer elements which comprise a piezoelectric composite material. By way of example, a piezoelectric composite material may be a composite comprising a piezoelectric ceramic (for example lead zirconate titanate) and a polymer (for example an epoxy resin or a polyurethane) (which may either also be piezoelectrically active or is a passive part of the piezoelectric composite material). In this case, piezoelectric ceramic features may regularly be embedded in a polymer matrix. For example, the piezoelectric composite material may be in the form of a plate (which has a substantially greater extent in two spatial directions than in the third spatial direction, which means that two extensive surface areas and one narrow side are formed).

In such a plate, the piezoelectric ceramic may be embedded in the polymer in the form of bars or tubes, said bars or tubes extending along the narrow side of the plate. In this configuration, a voltage can be applied across the narrow side by electrodes on the opposite (extensive) surface areas of the plate. As a result of the applied voltage, the piezoelectric ceramic features can produce ultrasound waves which depart in a direction perpendicular to the extensive surface areas of the plate.

Conversely, ultrasound waves which impinge perpendicular to the extensive surface areas of the plate can result in a voltage building up across the narrow side of the plate on account of the piezoelectric activity of the piezoelectric ceramic features. By measuring this voltage, it is possible to draw conclusions about a sound pressure of the incident ultrasound wave and/or of a surface area of the plate onto which the incident wave impinges.

Hence, the elements described in connection with FIG. 7 to FIG. 9 can be operated both as ultrasound transmitter elements and as ultrasound receiver elements given appropriate circuitry. By way of example, these elements can be used in the apparatuses shown in FIG. 2, FIG. 5 or FIG. 6.

In one preferred embodiment, a plate of a piezoelectric composite material may contain a composite comprising piezoelectric ceramic fibres and a polymer. This composite comprising piezoelectric ceramic fibres and a polymer consists of piezoelectric ceramic fibre bundles which are infiltrated with a polymer (for example an epoxy resin or a polyurethane). Plates of this composite can be manufactured in arbitrary shapes, for example with a round or rectangular outline. Typical volume proportions of the piezoelectric ceramic fibres are between 20 and 80%. The narrow side of the plate may have a thickness of between 100 µm and 5 cm, for example. The fibre diameter of the piezoelectric ceramic fibres may be between 50 µm and 1 mm. Such plates can be used to achieve resonant frequencies of between 20 kHz and 400 KHz, with the result that ultrasound transmitters and/or ultrasound receivers can be manufactured which operate using ultrasound in a frequency range between 20 kHz and 400 KHz. In this case, the respective resonant frequency can be stipulated by the thickness of the plate. Such piezoelectric ceramic fibre composite plates can be manufactured by cutting initial blocks of the material.

Each of FIG. 7 to FIG. 9 shows three views of an ultrasound transmitter element 3 and of a plurality of ultrasound receiver elements 2 . . . 2''' with a common ultrasound transducer element 22, 32. As already mentioned, however, it is possible for each of the elements shown also to be operated with the opposite function in each case. The top figures (FIG. 7a, FIG. 7d, FIG. 8a, FIG. 8d, FIG. 9a and FIG. 9d) show a schematic plan view of the respective element from the side which is averted from the material web for which the edge is intended to be detected during operation. The bottom figures (FIG. 7c, FIG. 7f, FIG. 8c, FIG. 8f, FIG. 9c and FIG. 9f) show a schematic plan view of the respective element from the side which faces the material web for which the edge is intended to be detected during operation. The middle figures (FIG. 7b, FIG. 7e, FIG. 8b, FIG. 8e, FIG. 9b and FIG. 9e) show a schematic view from the side (i.e. from a plane which runs parallel to a plane which contains the material web).

All of the elements shown in FIG. 7 to FIG. 9 have a continuous, two-dimensional electrode 23, 33 on the side which is averted from the material web in each case. The ultrasound transmitter elements 3 also have a continuous, two-dimensional electrode 31 on the side which faces the material web. Therefore, the ultrasound sensors in FIG. 7 to FIG. 9 each have just one ultrasound transmitter element which applies an ultrasound measurement signal to all of the ultrasound receiver elements.

The electrodes shown in FIG. 7 to FIG. 9 may consist of thin metal layers (for example gold or silver). These can be produced by popular thin layer deposition techniques, for example by sputtering. It is likewise possible for the electrodes to be produced by printing conductive materials (for example silver particles in solution).

FIGS. 7d to 7f show a first embodiment in which a patterned electrode forms a plurality of receiver regions 21a to 21n which form the ultrasound receiver elements 2 to 2'''. Each of the ultrasound receiver elements 2 to 2''' formed in this manner can have contact made with it in the respective receiver region 21a to 21n and can therefore be read separately. The ultrasound transducer element in FIG. 7d to FIG. 7f has a trapezoidal outline. The metallization on that side of the ultrasound transducer element which faces the material web is patterned by cutouts 24, said cutouts 24 running obliquely with respect to the direction of movement of the material web. This ensures that if the edge of the material web covers a marginal region of one ultrasound receiver element 2 to 2''' then it simultaneously also covers a marginal region of another ultrasound receiver element 2 to 2'''. This allows an increase in the sensitivity of the apparatus in the transition region between two ultrasound receiver elements 2 to 2'''.

If a material web covers a portion or an entire receiver region 21a to 21n, a measurement signal that can be tapped off from the respective region is reduced. This means that an evaluation circuit can be used to determine a position for the edge of the material web from the measurement signals from the ultrasound receiver elements 2 to 2'''.

Figure 8A:
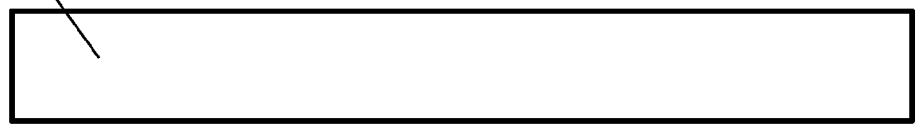
FIG. 8a to FIG. 8f show various schematic views of transmitter and ultrasound receiver elements.
Figure 8B:
Figure 8C:
Figure 8D:
Figure 8E:
Figure 8F:
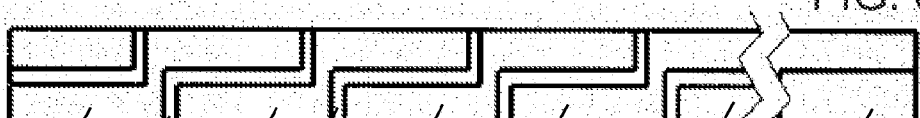

The ultrasound receiver elements 2 to 2''' shown in FIG. 8d to FIG. 8f are formed, like the ultrasound receiver elements 2 to 2''' shown in FIG. 7d to FIG. 7f, by cutouts 24 in a metallization on the side of the ultrasound transducer element that faces the material web. In FIG. 8e and FIG. 8f, however, each cutout 24 has a double-angled profile, with the cutout initially running parallel to the direction of movement of the material web, beginning from an edge of that side of the ultrasound transducer element which faces the material web. After a predetermined first length (for example half of the extent of that side of the ultrasound transducer element that faces the material web parallel to the direction of movement of the material web), the cutout bends to approximately 90° and then runs perpendicular to the direction of movement of the material web for a predetermined second length. The cutout 24 then bends to approximately 90° again and runs as far as the edge of that side of the ultrasound transducer element which faces the material web, which edge is opposite the starting edge. Hence, complexly shaped ultrasound receiver elements 2 to 2''' are formed, the surface of each of which has two rectangular regions which are connected to one another. With this geometry, the edge of the material web sweeps over two ultrasound receiver elements 2 to 2''' almost over the entire measurement range in any position, that is to say that the measurement ranges of adjacent ultrasound receiver elements 2 to 2''' overlap one another. Hence, it is almost always possible to use two measurement signals in order to detect the edge of the material web, which can increase the sensitivity of the measurement.

A further refinement of this principle is shown in FIG. 9e to FIG. 9f. In this case, the metallization of the side which faces the material web likewise has two bends, both of which are greater than 90°, however. The profile of the cutouts 24 is otherwise as shown in FIG. 8f. The bends with an angle of greater than 90° result in the edge of the material web sweeping over two ultrasound receiver elements 2 to 2''' over the entire measurement range in any position.

Beyond the geometries shown in FIG. 7 to FIG. 9, the ultrasound receiver elements 2 to 2''' can also be formed with other shapes. The manufacture can be effected by using shadow masks in the vapour deposition or sputtering process, as a result of which the shape of the mask allows almost any patterns of cutout to be produced. The same applies when a two-dimensional metallization is put on, and the cutouts are then written into the metallization, for example by using laser ablation techniques.

Figure 10:
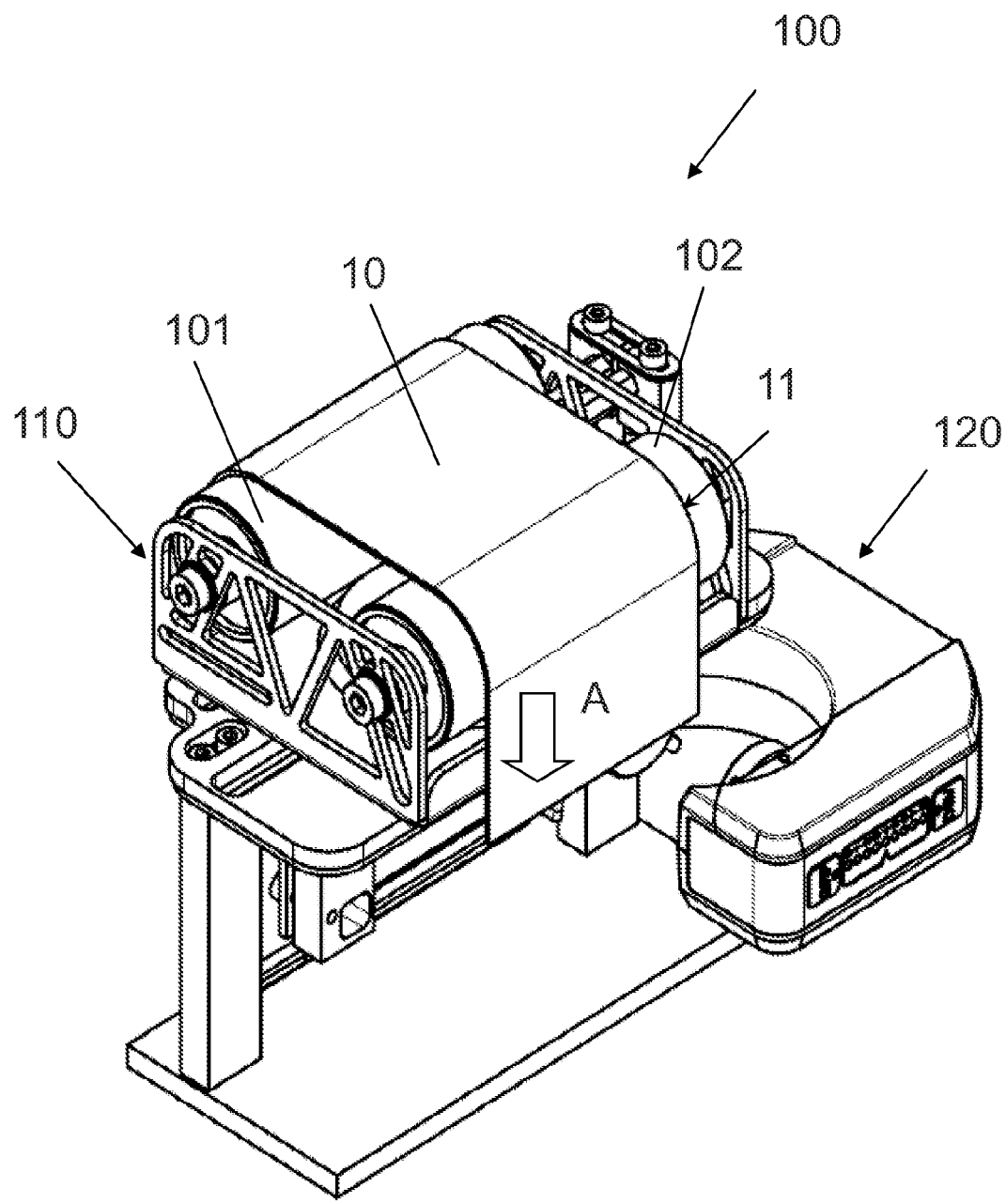
FIG. 10 shows an apparatus for detecting an edge of a material web and for correcting a detected offset.

FIG. 10 shows an apparatus 100 which, besides a sensor unit 120 (in this case the apparatuses from FIG. 2, FIG. 5 or FIG. 6 can be used, for example), furthermore also contains an apparatus for correcting a lateral offset 110 in the material web 10. The material web 10 runs in the direction of movement A, with an edge 11 of the material web running inside a measurement range of the sensor unit 120. This sensor unit 120 is designed to determine the position of the edge 11 of the material web 10 at a predetermined time (for example periodically or else continuously). The apparatus 100 has an evaluation circuit which receives the measurement signals from an ultrasound sensor of the sensor unit 120 and determines the position of the edge 11 of the material web 10 therefrom. If the ultrasound sensor has a plurality of ultrasound receiver elements, the evaluation circuit can evaluate the individual measurement signals in order to determine the position of the edge 11, as described above. By way of example, for each ultrasound receiver element, the evaluation circuit can resort to a table which stores the positions of the edge 11 that correspond to a particular measurement signal. By comparing a current measurement signal with the stored values, it is possible to determine the position of the edge 11. The evaluation circuit may be accommodated in the housing of the sensor unit 120, or else at other locations within the apparatus 100.

The position of the edge 11 of the material web 10 that has been determined by the evaluation circuit can then be used to ascertain a lateral offset in the material web from a stored setpoint position. This comparison can likewise be made in the evaluation circuit, or else in a further circuit. When the magnitude of a lateral offset has been determined, this magnitude can be used to feed the apparatus for correcting a lateral offset 110, which apparatus is designed to correct a lateral offset.

In the example in FIG. 10, the apparatus for correcting a lateral offset 110 comprises two rollers 101, 102 which are mounted so as to be able to rotate. Depending on the magnitude of the lateral offset, the two rollers 101, 102 are swivelled in order to correct the offset.

Even if the sensor unit 120 does not contain an apparatus for correcting a lateral offset, it can nevertheless comprise one or more rollers in order to guide the material web such that an edge of the material web runs through the measurement range of the sensor unit 120.

The invention claimed is:

1. An apparatus for detecting an edge of a material web, comprising:
   an ultrasound sensor which comprises an ultrasound receiver element and an ultrasound transmitter element, wherein at least one of:

the ultrasound transmitter element comprises a first ultrasound transducer element, or the ultrasound receiver element comprises a second ultrasound transducer element, and wherein at least one of the first or second ultrasound transducer element comprises a piezoelectric composite material, wherein the piezoelectric composite material comprises a material in which a piezoelectrically active material is integrally connected to a polymer.

2. An apparatus for detecting an edge of a material web, comprising:

an ultrasound sensor which comprises one or more separately readable ultrasound receiver elements and one or more separately actuatable ultrasound transmitter elements, wherein at least one of:

two or more ultrasound receiver elements have a first common ultrasound transducer element, or two or more ultrasound transmitter elements have a second common ultrasound transducer element.

3. The apparatus according to claim 1, wherein the one or more ultrasound transmitter elements and the one or more ultrasound receiver elements are arranged such that the material web can pass between the one or more ultrasound transmitter elements and the one or more ultrasound receiver elements, with the result that the one or more ultrasound transmitter elements and the one or more ultrasound receiver elements are arranged on different sides of the material web.

4. The apparatus according to claim 1, wherein the ultrasound sensor comprises three or four ultrasound receiver elements and one of the ultrasound transmitter elements is designed such that it applies an ultrasound measurement signal to three or four of the ultrasound receiver elements.

5. The apparatus according to claim 1, wherein each ultrasound receiver element has an associated measurement range in which it can detect the edge of the material web, and wherein the measurement ranges directly adjoin or overlap one another in a direction of measurement.

6. The apparatus according to claim 1, also comprising:

a housing which comprises a first and a second arm, wherein the one or more ultrasound transmitter elements are arranged on the first arm and the one or more ultrasound receiver elements are arranged on the second arm.

7. The apparatus according to claim 1, wherein at least one of the ultrasound transmitter element or the ultrasound receiver element comprises ultrasound transducer elements which comprise a piezoelectric composite material.

8. The apparatus according to claim 7, wherein the piezoelectric composite material is a piezoelectric fibre composite material which comprises a polymer and piezoelectric ceramic fibres.

9. The apparatus according to claim 1, wherein at least one of the ultrasound receiver element or the ultrasound transmitter element includes one or more ultrasound transducer elements of two-dimensional design.

10. The apparatus according to claim 9, wherein opposite surface areas of the ultrasound transducer elements of at least one of the ultrasound receiver element or the ultrasound transmitter element is provided with metallizations in order to make electrical contact with the one or more transducer elements.

11. The apparatus according to claim 10, wherein the metallizations of the receiver-end one or more ultrasound transducer elements are embodied such that a side of the receiver-end one or more ultrasound transducer elements that faces the ultrasound transmitter element has two or more non-contiguous receiver regions formed on it which can be read separately in order to form two or more of the ultrasound receiver elements.

12. The apparatus according to claim 11, wherein the metallizations of the transmitter-end one or more ultrasound transducer elements are embodied such that a side of the transmitter-end one or more ultrasound transducer elements that faces the ultrasound receiver element has two or more non-contiguous transmitter regions formed on it which can be actuated separately in order to form two or more ultrasound transmitter elements.

13. The apparatus according to claim 12, wherein at least one of:

the two or more non-contiguous receiver regions are formed by cutouts in the metallization, or the two or more non-contiguous transmitter regions are formed by cutouts in the metallization.

14. The apparatus according to claim 13, wherein the cutouts run at least to some extent obliquely, perpendicularly, or parallel to a direction of movement of the material web.

15. The apparatus according to claim 1, also comprising an evaluation circuit which is communicatively coupled to the ultrasound receiver element and is designed to ascertain a position for the edge of the material web from measurement signals that are received by the ultrasound receiver element.

16. The apparatus according to claim 15, also comprising:

a correction apparatus which is designed to alter the position of the edge of the material web on the basis of a comparison of a position signal produced by the evaluation circuit with a setpoint position signal.

17. The apparatus according to claim 1, also comprising:

an apparatus for guiding the material web, wherein the ultrasound sensor is arranged such that it can detect the edge of a material web in a predetermined measurement range.

18. The apparatus according to claim 1, also comprising an evaluation circuit which is communicatively coupled to the ultrasound receiver element and is configured to ascertain a position for a first edge of the material web and for a second edge of the material web from measurement signals that are received by the ultrasound receiver element.

19. The apparatus according to claim 1, also comprising an evaluation circuit which is communicatively coupled to the ultrasound receiver element and is designed configured to ascertain a width of a material web from measurement signals that are received by the ultrasound receiver element.

20. The apparatus according to claim 1, also comprising:

a housing which comprises a first and a second arm, wherein the first ultrasound transducer element and the second ultrasound transducer element are arranged on both arms.

21. The apparatus according to claim 1, wherein the ultrasound transmitter element and the ultrasound receiver element are arranged on the same side of a material web when the apparatus is operational.

22. The apparatus according to claim 21, also comprising a reflector which is designed to reflect at least a portion of an ultrasound signal emitted by the ultrasound transmitter element in the direction of the ultrasound receiver element.

23. The apparatus according to claim 1, wherein the ultrasound transmitter element is designed to also act as an ultrasound receiver element.

24. The apparatus according to claim 12, wherein at least one of the two or more non-contiguous receiver regions or the two or more non-contiguous transmitter regions are formed by cutouts in the metallization.

\* \* \* \* \*

UNITED STATES PATENT AND TRADEMARK OFFICE
CERTIFICATE OF CORRECTION

PATENT NO. : 9,238,563 B2  
APPLICATION NO. : 13/871834  
DATED : January 19, 2016  
INVENTOR(S) : Lars Zwerger, Wolfgang Krauth and Günter Franz Page 1 of 1

It is certified that error appears in the above-identified patent and that said Letters Patent is hereby corrected as shown below:

Specification

In Column 1, In Line 52, Delete "20 mm)" and insert -- 20 mm). --, therefor.

Claims

In Column 16, In Line 2, In Claim 11, before "ultrasound" delete "of the".

In Column 16, In line 46, In Claim 19, before "configured" delete "designed".

Signed and Sealed this  
Twelfth Day of April, 2016

Michelle K. Lee  
*Director of the United States Patent and Trademark Office*